United States Patent [19]

Hoffman et al.

[11] Patent Number: 5,053,525

[45] Date of Patent: Oct. 1, 1991

[54] OXO-ANALOGS OF MEVINOLIN-LIKE ANTIHYPER-CHOLESTEROLEMIC AGENTS

[75] Inventors: William F. Hoffman; Ta J. Lee, both of Lansdale; Gerald E. Stokker, Gwynedd Valley, all of Pa.

[73] Assignee: Merck & Co., Inc., Rahway, N.J.

[21] Appl. No.: 828,817

[22] Filed: Feb. 13, 1986

Related U.S. Application Data

[63] Continuation of Ser. No. 550,707, Nov. 14, 1983, abandoned.

[51] Int. Cl.$^5$ ................................................ C07C 9/76
[52] U.S. Cl. ..................................... 560/107; 560/45; 560/48; 560/53; 560/119; 562/455; 562/462; 260/410.5; 514/533; 514/534; 514/824; 514/540

[58] Field of Search ...................... 560/107, 45, 48, 53, 560/119; 562/455, 462; 260/410.5; 514/533, 534, 824, 540

[56] References Cited

FOREIGN PATENT DOCUMENTS 55-59140 5/1980 Japan .

OTHER PUBLICATIONS

Sato, A. et al., Chem. Pharm. Bull., 28(5), 1509–1525, 1980.

*Primary Examiner*—Paul J. Killos
*Attorney, Agent, or Firm*—Melvin Winokur; Joseph F. DiPrima

[57] ABSTRACT

Mevinolin-like compounds in which the lactone is opened and the hydroxyl function produced thereby is replaced by an oxo function are potent HMG-CoA reductase inhibitors possessing one less asymmetric center.

9 Claims, No Drawings

OXO-ANALOGS OF MEVINOLIN-LIKE ANTIHYPER-CHOLESTEROLEMIC AGENTS

This is a continuation of application Ser. No. 550,707, filed Nov. 14, 1983.

SUMMARY OF THE INVENTION

This invention is concerned with novel compounds of structural formula I:

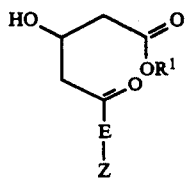

wherein Z is a variety of mono- and bi-carbocylcic moieties with various substituents well known to those skilled in the art of 3-hydroxy-3-methylglutaryl Coenzyme A (HMG-CoA) reducatse inhibitors useful in the treatment of familial hypercholesterolemia, hyperlipemia, and atherosclerosis.

The invention is also concerned with novel processes for the preparation of the novel compounds; pharmaceutical formulations comprising a novel compound as active ingredient; and a method of treating familial hypercholesterolemia, hyperlipemia, and atherosclerosis.

BACKGROUND OF THE INVENTION

Over the past several years a number of structurally related antihypercholesterolemic agents acting by inhibition of HMG-CoA reductase have been reported in the patent literature and elsewhere. The compounds have varied from the natural fermentation products, compactin and mevinolin,

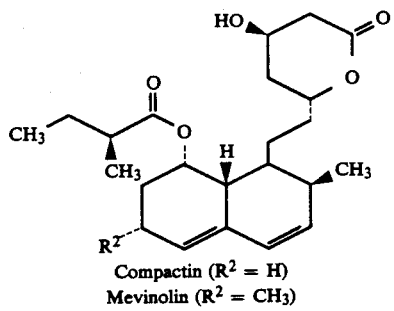

Compactin ($R^2$ = H)
Mevinolin ($R^2$ = $CH_3$)

to di- and tetrahydro derivatives thereof; to analogs with different esters in the 8-position of the polyhydronaphthalene moiety, to totally synthetic analogs, wherein the polyhydronaphthalene moiety is replaced by substituted mono- and bicyclic aromatics, and biphenyls. But in all instances the active compound included a 4-hydroxytetrahydropyran-2-one ring or the corresponding 3,5-dihydroxy acid, or derivatives thereof, formed by opening the pyranone ring such as:

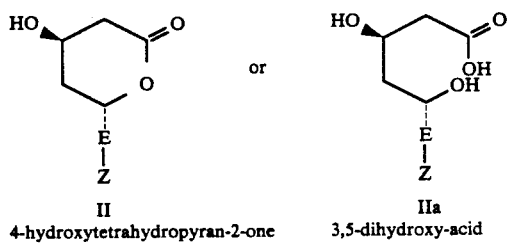

II
4-hydroxytetrahydropyran-2-one

IIa
3,5-dihydroxy-acid

In all of these compounds the 3,5-dihydroxy acid or corresponding lactone moiety is present and the particular stereochemistry depicted is essential for manifestation of the optimum enzyme inhibitory activity.

Now with the present invention there are provided compounds structurally related to those lactones and dihydroxy acids that do not have the 5-hydroxy functionality, do not form a lactone ring, and are incapable of stereochemical variation at the 5-position of the acid because the 5-carbon is not asymmetric. On the contrary, the 5-carbon carries an oxo function which greatly facilitates the total synthesis of active compounds in that by eliminating one asymmetric center it is unnecessary to separate diastereoisomers or to conduct a stereoselective synthesis to obtain optimum enzyme inhibitory activity. It is believed that structures I are reduced in situ to generate the "active" inhibitors of structure II or IIa.

The active compounds of this invention are useful in either the racemic form or as the 3(R)-isomer. Those compounds produced by total synthesis are obtained initially as racemates, but may be resolved by standard methods into 3(R)- and (S)-isomers. Compounds of Structure I which are synthesized starting from natural fermentation products such as mevinolin and its analogs are obtained as the optically pure 3(R)-isomers.

DETAILED DESCRIPTION OF THE INVENTION

The novel compounds of this invention have structural formula:

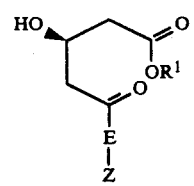

wherein
$R^1$ is
1) hydrogen,
2) $C_{1-4}$alkyl,
3) 2,3-dihydroxypropyl,
4) alkali metal cation, such as $Na^+$, or $K^+$, or
5) ammonium of formula $N^+R^3R^4R^5R^6$ wherein $R^3$, $R^4$, $R^5$ and $R^6$ are independently hydrogen or $C_{1-4}$alkyl or two of $R^3$, $R^4$, $R^5$ and $R^6$ are joined together to form a 5 or 6-membered heterocycle such as pyrrolidino or piperidino with the nitrogen to which they are attached;

E is $-CH_2CH_2-$, $-CH=CH-$, or $(CH_2)_3-$; and
Z is

1)
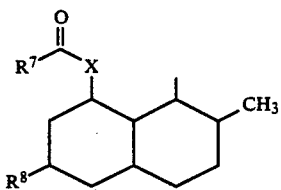

wherein the dotted lines represent all of the possible oxidation states of the bicyclic system such as naphthalene, dihydro-, tetrahydro-, hexahydro-, octahydro-, and decahydronaphthalene;

X is —O— or >NR$^9$ wherein
R$^9$ is H or C$_{1-3}$alkyl;
R$^7$ is C$_2$-alkyl; and
R$^8$ is H or —CH$_3$;

2)
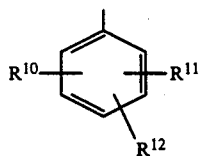

wherein R$^{10}$, R$^{11}$ and R$^{12}$ are independently
   a) hydrogen,
   b) halogen, such as bromo, chloro or fluoro,
   c) C$_{1-4}$alkyl,
   d) halo-C$_{1-4}$alkyl,
   e) phenyl either unsubstituted or substituted with one or more of
      i) C$_{1-4}$alkoxy,
      ii) C$_{1-4}$alkyl,
      iii) C$_{2-8}$alkanoyloxy, or
      iv) halo-C$_{1-4}$alkyl,
      v) halo, such as bromo, chloro or fluoro,
   f) wherein R$^{13}$ is
      i) hydrogen,
      ii) Cl
      iii) benzoyl,
      iv) phenyl,
      v) halophenyl,
      vi) phenyl-C$_{1-3}$alkyl, either unsubstituted or substituted with one or more of halogen, C$_{1-4}$alkoxy, C$_{1-4}$alkyl or halo-C$_{1-4}$alkyl,
      vii) C$_{1-9}$alkyl,
      viii) cinnamyl,
      ix) halo-C$_{1-4}$alkyl,
      x) allyl,
      xi) C$_{3-6}$cycloalkyl-C$_{1-3}$alkyl,
      xii) adamantyl-C$_{1-3}$alkyl, 3)
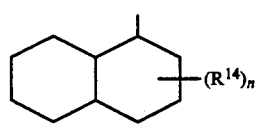

wherein n is 0-2, and is halo such as chloro, bromo or fluoro, or C$_{1-4}$ alkyl, and 4)
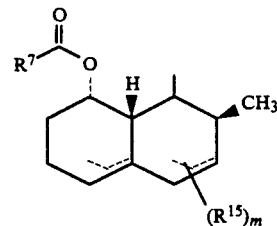

wherein the dotted lines represent possible double bonds there being 0, 1 or 2 double bonds; m represents 1, 2 or 3; and
R$^{15}$ is
   1) methyl,
   2) hydroxy,
   3) C$_{1-4}$ alkoxy,
   4) oxo or
   5) halo.

Preferred embodiments of the novel compounds are those in which:
R$^1$ is hydro9en, an alkali metal cation or an ammonium cation;
E is —CH=CH— or —CH$_2$CH$_2$—; and
Z is 1)
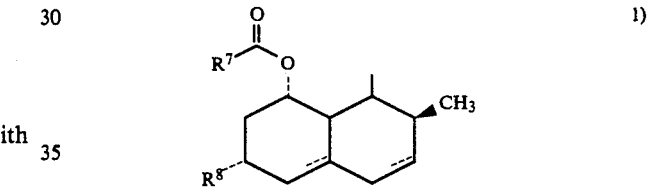

wherein

is 2-methylbutyryl or 2,2-dimethylbutyryl;

2)
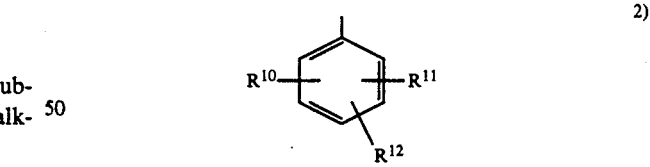

wherein R$^{10,}$ R$^{11}$ and R$^{12}$ are independently
   a) halogen,
   b) C$_{1-4}$alkyl,
   c) halo-C$_{1-4}$alkyl,
   d) phenyl with 1 to 3 substituents selected from halo, C$_{1-4}$alkyl or C$_{1-4}$alkoxy,
   e) OR$^{13}$, wherein Rhu 13 is
      i) phenyl,
      ii) halophenyl,
      iii) phenyl substituted with 1-3 substituents selected from halogen, and C$_{1-4}$alkyl,
      iv) phenyl-C$_{1-3}$ alkyl, either unsubstituted or substituted with one or more of halogen, C$_{1-4}$ alkoxy, C$_{1-4}$ alkyl or halo-C$_{1-4}$ alkyl; or

3)

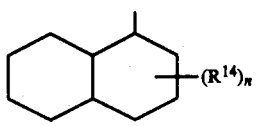

wherein n is 0, 1 or 2 and is methyl and the ring system is naphthalene or 5,6,7,8-tetrahydronaphthalene.

One novel process for preparing the novel compounds of this invention is particularly useful when starting with compounds with a pre-formed 4-hydroxytetrahydropyran-2-one moiety or the corresponding 3,5-dihydroxy acid and is illustrated as follows:

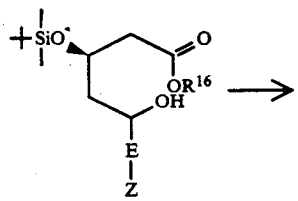

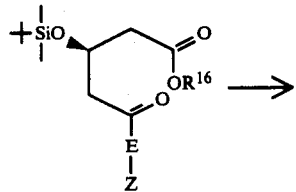

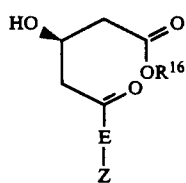

wherein $R^{16}$ is C alkyl, especially methyl. After protecting the 4-hydroxyl of the lactone with a dimethyl-tert-butylsilyl group and preparing an alkyl ester by known procedures, the resulting 5-hydroxy of the open-chain acid is oxidized to the ketone. Suitable oxiding agents include: pyridinium chlorochromate in a chlorinated alkane such as methylene chloride or chloroform at about 0° to about 25° C. for about 1 to 4 hour; oxalyl chloride in dimethylsulfoxide at about −70° to about −40° C. for about 0.25 to 0.5 hours; trifluoroacetic anhydride in dimethylsulfoxide at about −70° to −40° C. for about 0.25 to 0.5 hour; and pyridinium dichromate in dimethyl formamide at 0° to 25° C. for 1 to 8 hours.

The silyl ether group is then hydrolyzed by treatment with acetic acid and tetrabutylammonium fluoride in tetrahydrofuran.

A related procedure is available for preparing compounds of this invention wherein E represents —CH$_2$CH$_2$—. It obviates the need for protection of the 3-hydroxy group before oxidizing the 5-hydroxy and is represented as follows:

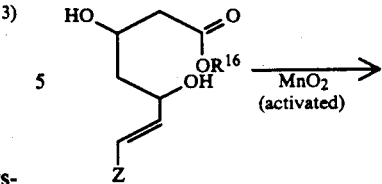

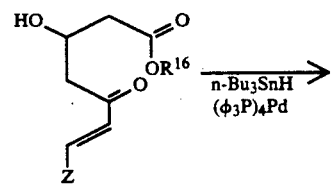

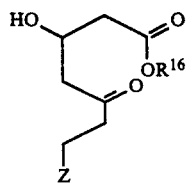

In the first step the dihydroxy compound is treated with activated manganese dioxide in a chlorinated hydrocarbon such as chloroform, methylene chloride, 1,2-dichloroethane or the like at about 0° C. to 40° C. preferably at ambient temperature for about 15 to 30 hours. The 5-oxo compound produced is then treated with tri-n-butyltin hydride and tetrakis(triphenyl-phosphine) palladium(0) in an ethereal solvent such as ether, THF, 1,2-dimethoxyethane or the like, at about ambient temperature for about 15 to 30 hours.

Alternatively, if the 3-hydroxy-5-oxocarboxylic acid moiety is being synthesized, the 5-oxo group is realized directly by a process which is another embodiment of this invention and which is exemplified as follows:

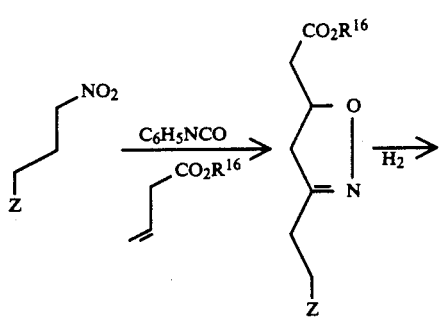

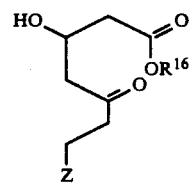

The nitro compound is treated with a $C_{1-4}$alkyl 3-butenoate, preferably methyl 3-butenoate, and an aromatic isocyanate such as p-toluoyl isocyanate, p-chlorophenyl isocyanate, phenyl isocyanate or the like, preferably the latter, and a bit of triethylamine as a catalyst in an inert organic solvent such as toluene, benzene, xylene, or the like at about 15° to 30° C., preferably about room temperature for about 5 to about 24 hours.

The resulting isoxazoline is reduced catalytically with palladium on carbon, platinum oxide or the like in an inert organic solvent such as a $C_{1-3}$alkanol, acetic acid or the like containing a little water in the presence of boric acid at about 15° to 30° C. and about 1–2 atmospheres of hydrogen pressure for about 1 to 6 hours.

The ester resulting from either of the foregoing synthetic schemes is readily saponified to the corresponding carboxylic acid salt by treatment with aqueous alkali such as potassium or sodium hydroxide to form the potassium or sodium salt respectively or with a quaternary ammonium hydroxide of formula $HONR^3R^4R^5R^6$ wherein none of the R groups is hydrogen to form the quaternary ammonium salt.

Acidifying any of these salts with a mineral acid results in the formation of the free carboxylic acid.

The acids are readily converted back to salts by treatment with the appropriate base or to esters by treatment with a $C_{1-4}$alkanol in the presence of a catalytic amount of an acid such as hydrogen chloride at about 50° to 100° C. for about 3 to 6 hours.

The previously described salts are converted back to esters by treatment with an alkyl halide such as 2,3-dihydroxypropyl iodide in an aprotic solvent such as N,N-dimethylformamide, N-methylpyrrolidone or hexamethylphosphoramide at about 25° to 100° C. for about 18 to 36 hours.

Those compounds, wherein Z is of the subtype (4), i.e., in which the polyhydronaphthalene moiety is substituted with hydroxy or oxo, halo or alkoxy are prepared from the corresponding substrate in which the 5-oxo group of the heptenoic acid is already in place. The processes, as applied to the -hydroxy analogs or the corresponding lactones, are disclosed in EP application 76601, British patents 2,111,052 and 2,075,013, EP application 74222, and Japanese published applications J58010572 and J57155995. Using those processes there are produced the following compounds:

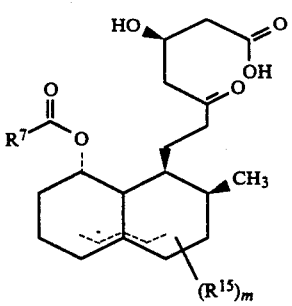

| Double Bonds | $R^7$ | $(R^{15})_m$ |
|---|---|---|
| 3,4:4a,5 | 1-methylpropyl | 6—OH |
| 3,4:4a,5 | 1,1-dimethylpropyl | 6—OH |
| 4,4a | 1-methylpropyl | 3—OH, 5—OH |
| 4,4a | 1,1-dimethylpropyl | 3—OH, 5—OH |
| 4,4a:5,6 | 1-methylpropyl | 3—OH |
| 4,4a:5,6 | 1,1-dimethylpropyl | 3—OH |
| — | 1-methylpropyl | 6—OH |
| — | 1,1-dimethylpropyl | 6—OH |
| — | 1-methylpropyl | 3—OH |
| — | 1,1-dimethylpropyl | 3—OH |
| 4,4a | 1-methylpropyl | 6—OH |
| 4,4a | 1,1-dimethylpropyl | 6—OH |
| 4,4a | 1-methylpropyl | 3—OH |
| 4,4a | 1,1-dimethylpropyl | 3—OH |
| 4a,5 | 1-methylpropyl | 6—OH |
| 4a,5 | 1,1-dimethylpropyl | 6—OH |

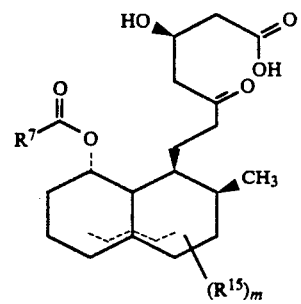

| Double Bonds | $R^7$ | $(R^{15})_m$ |
|---|---|---|
| 4a,5 | 1-methylpropyl | 3—OH |
| 4a,5 | 1,1-dimethylpropyl | 3—OH |
| 4,4a | 1-methylpropyl | 3—OH, 5=O |
| 4,4a | 1,1-dimethylpropyl | 3—OH, 5=O |
| 4,4a | 1-methylpropyl | 3=O, 5=O |
| 4,4a | 1,1-dimethylpropyl | 3=O, 5=O |
| — | 1-methylpropyl | 3—OH, 5—OH |
| — | 1,1-dimethylpropyl | 3—OH, 5—OH |
| 4,4a | 1-methylpropyl | 3—Cl, 5—Cl |
| 4,4a | 1,1-dimethylpropyl | 3—Cl, 5—Cl |
| 4,4a | 1-methylpropyl | 3—OCH$_3$, 5—OH |
| 4,4a | 1,1-dimethylpropyl | 3—OCH$_3$, 5—OH |
| 4,4a | 1-methylpropyl | 3—OC$_2$H$_5$, 5—OH |
| 4,4a | 1,1-dimethylpropyl | 3—OC$_2$H$_5$, 5—OH |
| 4,4a | 1-methylpropyl | 3—OC$_4$H$_9$, 5—OH |
| 4,4a | 1,1-dimethylpropyl | 3—OC$_4$H$_9$, 5—OH |
| 4,4a | 1-methylpropyl | 6—CH$_3$, 3—OH, 5—OH |
| 4,4a | 1,1-dimethylpropyl | 6—CH$_3$, 3—OH, 5—OH |

The novel pharmaceutical composition of this invention comprises at least one of the compounds of formula I in association with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations.

A typical capsule for oral administration contains active ingredient (25 mg), lactose (75 mg) and magnesium stearate (15 mg). The mixture is passed through a 60 mesh sieve and packed into a No. 1 gelatin capsule.

A typical injectable preparation is produced by asceptically placing 25 mg of a water soluble salt of sterile active ingredient into a vial, aseptically freeze-drying and sealing. For use, the contents of the vial are mixed with 2 ml of physiological saline, to produce an injectable preparation.

The novel method of treating atherosclerosis, familial hypercholesterolemia, or hyperlipemia of this invention comprises administration of an effective antihypercholesterolemic amount of a compound of Formula I to a patient in need of such treatment.

The dose to be administered depends on the unitary dose, the symptoms, and the age and the body weight of the patient. A dose for adults is preferably between 20 and 2,000 mg per day, which can be administered in a single dose or in the form of individual doses from 1–4 times per day.

The compounds of this invention also have useful antifungal activities. For example, they may be used to control strains of Penicillium sp., *Aspergillus niger*, , Cladosporium sp., *Cochliobolus miyabeorus* and *Helminthosporium cynodnotis*. or those utilities they are ad-

EXAMPLE 1

7-[2(S),6(R)-Dimethyl-8(S)-(2(S)-methylbutyryloxy)-1,2,6,7,8,8a(R)-hexahydro-1(S)-naphthyl]-3(R)-hydroxy-5-oxoheptanoic acid Step A: Preparation of 6(R)-[2-(8(S)-(2(S)-methylbutyryloxy)-2(S),6(R)-dimethyl-1,2,6,7,8,8a(R)-hexahydronaphthyl-1(S))-ethyl]-4(R)-(dimethyl-tert-butylsilyloxy)-3,4,5,6-tetrahydro-2H-pyran-2-one Mevinolin (4.04 g, 0.01 mol) was dissolved in 25 ml of dry dimethylformamide (DMF) and treated with 2.7 g (0.04 mol) of imidazole and 3 g (0.02 mol) of dimethyl-tert-butylsilyl chloride, and the solution was stirred under nitrogen overnight. The mixture was poured into 200 ml of ether, washed with 2×50 ml of water, 1×25 ml of 1N hydrochloric acid, 1×25 ml of saturated aqueous sodium carbonate and 2×50 ml of brine, dried over MgSO4 and concentrated to dryness. The residue was chromatographed on a "Still" column of silica gel (6.0×17.7 cm, 230–400 mesh) by elution with 45% ether in hexane (V/V) collecting 20 ml fractions. The fractions containing the product (21–52) were combined and concentrated to dryness to give 5.2 of oil.

Step B: Preparation of Methyl 7-[2(S), 6(R)-Dimethyl-8(S)-(2(S)-methylbutyryloxy)-1,2,6,7,8,8a(R)-hexahydro-1(S)-naphthyl]-3(R)-(tert-butyldimethylsilyloxy)-5(R)-hydroxyheptanoate The silyl ether from Step A (1.03 g, 0.002 mol) was dissolved in 10 ml of methanol, treated with 2 ml of 1N aqueous sodium hydroxide and the mixture was stirred for 2 hours at room temperature. The methanol was evaporated under reduced pressure and the residue was freed of water by azeotropic distillation of 4×10 ml of toluene. The solid residue was dissolved in 5 ml of dry DMF, treated with 300 μl, (0.68 g, 0.0048 mol) of methyl iodide and the mixture was stirred overnight at room temperature. The mixture was poured into 100 ml of ether and washed with 20 ml of water and 20 ml of brine, dried (MgSO4) and concentrated to dryness to give 1.0 g of residue (contained DMF). This material was chromatographed on a "Still" column of silica gel (6.0×17.7 cm, 230–400 mesh) by elution with 45% ether in hexane (V/V) collecting 20 ml fractions. Fractions 32–50 containing the major component were combined and concentrated to dryness to give 576 mg of oily product.

Step C: Preparation of Methyl 7-[2(S), 6(R)-Dimethyl-8(S)-(2(S)-methylbutyryloxy)-1,2,6,7,8,8a(R)-hexahydro-1(S)-naphthyl]-3(R)-(tert-butyldimethylsilyloxy)-5-oxoheptanoate The ester from Step B (586 mg, 0.001 mol) was dissolved in 10 ml of methylene chloride and cooled to 0° C. Pyridine chlorochromate (0.56 g, 0.0026 mol) was added and the stirred mixture was allowed to warm spontaneously over 2 hours. Additional pyridine chlorochromate (224 mg, 0.001 mol) was added and stirring was continued another hour. The methylene chloride was evaporated in vacuo. The residue was suspended in 5 ml. ether, placed on top of a 4×40 cm column of silica gel (70–230 mesh) and eluted with 40% ether in hexane (V/V) collecting 15 ml fractions. Fractions 10–23 were combined and concentrated to 130 mg. of oily product.

Step D: Preparation of Methyl 7-[2(S), 6(R)-Dimethyl-8(S)-(2(S)-methylbutyryloxy)-1,2,6,7,8,8a(R)-hexahydro-1(S)-naphthyl]-3(R)-hydroxy-5-oxoheptanoate The silyl ether from Step C (230 mg, 0.00024 mol) was dissolved in 5 ml of tetrahydrofuran (THF) and treated with 54 μl, (0.057 g, 0.00095 mol) of acetic acid and 710 μl (1M in THF, 0.00071 mol) of tetrabutylammonium fluoride (Bu4N F) and the mixture was stirred overnight at room temperature. Another 57 μl of acetic acid and 710 μl of Bu4N F were added and stirring was continued an additional 24 hours. The mixture was poured into 100 ml of ether and washed with 1×5 ml of 1N hydrochloric acid, 1×10 ml of saturated aqueous sodium bicarbonate and 2×10 ml of brine and dried (MgSO4) Concentration to dryness gave 120 mg of an oil. The oil was chromatographed on a "Still" column of silica gel (1.5×17.7 cm, 230–400 mesh) by elution with 5% acetone in methylene chloride (v/v) collecting 5 ml fractions. Fractions 12–20 containing the product were combined and concentrated to dryness to give 53 mg of solid (m.p. 64°–66° C.). Recrystallization of a sample from hexane gave material with m.p. 67°–68° C.

Analysis for C (434.55): Calc: C, 69.09; H, 8.81. Found: C, 69.30; H, 9.38.

Step E: Preparation of 7-[2(S),6(R)-Dimethyl-8(S)-(2(S)-methylbutyryloxy)-1,2,6,7,8,8a(R)-hexahydro-1(S)-naphthyl]-3(R)-hydroxy-5-oxoheptanoic acid The ester from Step D (43 mg, 0.0001 mol) was dissolved in 5 ml of methanol and treated with 2 ml of 0.1N sodium hydroxide (0.0002 mol) and stirred overnight at room temperature. The methanol was evaporated in vacuo and the residue was acidified with 1N hydrochloric acid and extracted with ether. The ether extract was washed with 3×10 ml of brine and dried over MgSO4. Concentration to dryness provided 36 mg of solid which after recrystallization from ether/hexane had m.p. 102°–103° C.

Analysis for (420.53): Calc: C, 68.54; H, 8.63. Found: C, 68.57; H, 8.88.

Employing the procedure substantially as described in Example 1, Steps A through E, but substituting for the mevinolin used in Step A, equimolar amounts of the lactones described in Table I there are produced the corresponding 5-oxocarboxylic acids, salts, and esters also described in Table I in accordance with the following reaction scheme:

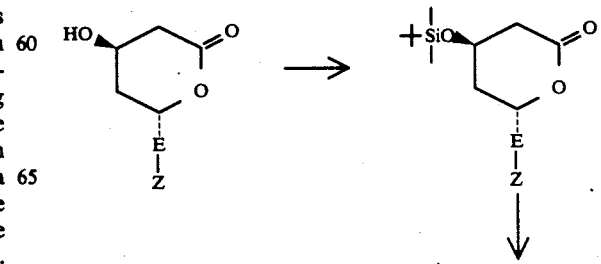

-continued

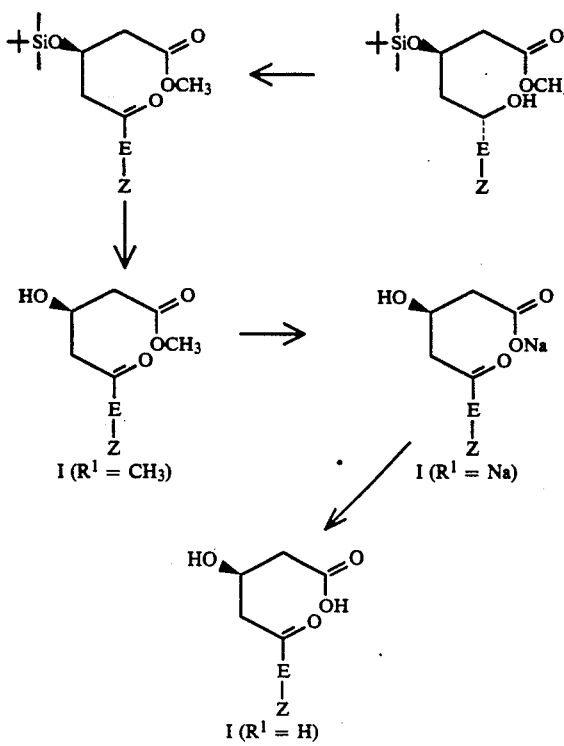

I ($R^1$ = CH$_3$)

I ($R^1$ = Na)

I ($R^1$ = H)

TABLE I (1)

| R$^7$C(O)— | R$^8$ | X | a | b |
| --- | --- | --- | --- | --- |
| 2(S)-methylbutyryl | —CH$_3$ | O | single | double |
| 2(S)-methylbutyryl | —CH$_3$ | O | single | single |
| 2(R)-methylbutyryl | —CH$_3$ | O | double | double |
| 2,2-dimethylbutyryl | —CH$_3$ | O | double | double |
| 2,2-dimethylbutyryl | —CH$_3$ | O | single | double |
| 2,2-dimethylbutyryl | —CH$_3$ | O | single | single |
| acetyl | —CH$_3$ | O | double | double |
| 2(S)-methylbutyryl | H | O | single | single |
| 2,2-dimethylbutyryl | H | O | double | double |
| 2,2-dimethylbutyryl | H | O | single | single |
| 2,2-dimethylbutyryl | —CH$_3$ | NH | single | single |
| 2-methyl-2-ethylbutyryl | —CH$_3$ | NH | single | single |
| 2-methylbutyryl | —CH$_3$ | NH | single | single |
| 4-fluorobenzoyl | —CH$_3$ | NH | single | single |
| 4-fluorophenylacetyl | —CH$_3$ | NH | single | single |
| 4-tert-butylbenzoyl | —CH$_3$ | NH | single | single |
| acetyl | —CH$_3$ | NH | double | double |
| acetyl | —CH$_3$ | NCH$_3$ | single | single |
| 2,2-dimethylbutyryl | —CH$_3$ | NCH$_3$ | single | single |
| 2,2-dimethylbutyryl | —CH$_3$ | NH | double | double |

(2)

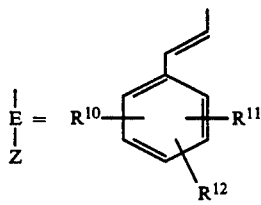

TABLE I-continued

| R$^{10}$ | R$^{11}$ | R$^{12}$ |
| --- | --- | --- |
| 6-(4-fluoro-3-methylphenyl)- | 2-methyl | 4-methyl |
| 6-(4-fluorophenyl)- | 2-chloro | 4-chloro |
| 6-(4-chlorophenyl)- | 2-chloro | 4-chloro |
| 6-(3,4-dichlorophenyl)- | 2-chloro | 4-chloro |
| 6-(4-fluoro-3-methylphenyl)- | 2-chloro | 4-chloro |
| 6-(3,4-dichlorophenyl)- | 2-methyl | 4-methyl |
| 6-(3,5-dimethylphenyl)- | 2-chloro | 4-chloro |
| 6-(3,4-dichlorophenyl)- | 2-methyl | 5-methyl |
| 6-(4-fluorophenyl)- | 2-methyl | 4-methyl |
| 6-(4-fluoro-3-methylphenyl)- | 2-methyl | 4-chloro |
| 6-(4-fluorobenzyloxy) | 2-chloro | 4-chloro |
| 6-(4-fluoro-3-methylphenyl) | 2-chloro | 4-methyl |

(3)

$$\underset{Z}{\overset{|}{\underset{|}{E}}} = \text{(decahydronaphthyl with propyl)} -(R^{14})_n$$

| n | R$^{14}$ | |
| --- | --- | --- |
| 1 | 2-methyl | naphthyl |
| 0 | — | naphthyl |
| 2 | 2,6-dimethyl | naphthyl |
| 1 | 2-methyl | 5,6,7,8-tetrahydronaphthyl |

EXAMPLE 2

7-(4'-Fluoro-3,3',5-trimethyl-[1,1'-biphenyl]-2-yl-3-hydroxy-5-oxoheptanoic acid Step A: Preparation of Methyl 3-(4'-Fluoro-3,3',5-o trimethyl-[1,1'biphenyl]-2-yl)propionate A solution of 1.716 g (13 mmol) of dimethyl malonate in 5 ml of DMF was added dropwise to a stirred suspension of sodium hydride (50% oil dispersion, 0.624 g, 13 mmol) in 15 ml of DMF and stirring was continued under nitrogen for 0.5 hour. The mixture was treated with ice bath cooling, with a solution of 3.1 g (11.8 mmol) of 2-chloromethyl-4'- o fluoro-3,3',5-trimethyl-1,1'-biphenyl in 10 ml of DMF. The resulting mixture was stirred at 0° C. for 10 minutes, at room temperature for 0.5 hour, and heated on a steam bath for 1 hour. Sodium chloride (0.759 g, 13 mmol) and 0.234 ml (13 mmol) of water were added to the reaction mixture and it was heated at reflux for 16 hours. The reaction mixture was cooled, poured into cold water and extracted with ether twice. The combined extracts were washed with dilute hydrochloric acid, dried over MgSO4, filtered and concentrated to dryness in vacuo to give 3.42 (11.38 mmol, 96%) of the desired product as a brown oil which was used directly in the next step without purification.

nmr (CDCl$_3$) δ: 2.27 (6H, a methyl singlet and a methyl doublet), 2.3 (2H, m), 2.34 (3H, s), 2.9 (2H, m), 3.60 (3H, s), 6.84 (H, bs), 7.1–7.2 (4H, m).

Step B: Preparation of 3-(4'-fluoro-3,3',5-trimethyl [1,1'-biphenyl]-2-yl)propanol A solution of 3.42 g (11.4 mmol) of the ester from Step A in 25 ml of ether was added dropwise to a stirred suspension of 0.38 g (10 mmol) of lithium aluminum hydride in 75 ml of ether at 0° C. under nitrogen. After completion of the addition, the mixture was stirred at room temperature for 15 minutes, refluxed for 1 hour, cooled in ice and treated with successive additions of 0.4 ml of water, 0.35 ml of 20% (w/v) aqueous sodium hydroxide and 1.1 ml of water. The resulting mixture was stirred at 0° C. for 0.5 hour, treated with anhydrous MgSO4, stirred for 15 minutes and filtered. The filtrate was concentrated in vacuo to give 3.08 g (11.3 mmol) (99%) of pale yellow oily product which was used directly in the next step without purification.

nmr (CDCl3) δ: 1.45-1.7 (2H, m), 2.25 (6H, s), 2.33 (3H, s), 2.45-2.7 (2H, m), 3.45 (2H, t, J=6Hz), 6.85 (H, bs), 6.95-7.2 (4H, m).

Step C: Preparation of 2-(3-Bromopropyl)-4'-fluoro-3,3',5-trimethyl-1,1'-biphenyl A solution of 1.08 g (4 mmol) of PBr3 in 10 ml of ether was added dropwise to a stirred solution of 3.08 g (11.3 mmol) of the alcohol from Step B in 40 ml of ether at 0° C. The mixture was stirred at room temperature for 1 hour, refluxed for 0.5 hour, cooled to room temperature, poured into ice water and extracted with ether. The extract was washed with water and saturated aqueous sodium bicarbonate, dried over MgSO4, filtered and evaporated to dryness in vacuo. The residue was purified by flash chromatography on silica gel (230-400 mesh) by elution with methylene chloride/hexane (1:3, v/v). Combination and evaporation of the appropriate fractions gave the desired bromide as a pale yellow oil, (1.9 g, 5.67 mmol, 48% overall Steps A, B and C).

nmr (CDCl3) δ: 1.7-2.0 (2H, m), 2.27 (6H, a methyl singlet and a methyl doublet), 2.35 (3H, s), 2.55-2.8) 5 (2H, m), 3.23 (2H, t, J=6Hz), 6.85 (H, bs), 6.95-7.2 (4H, m).

Step D: Preparation of 4'-Fluoro-3,3',5-trimethyl-2-(3-nitropropyl)-1,1'-biphenyl A solution of 1.90 g (5.66 mmol) of the bromopropyl compound from Step C in 5 ml of ether was added to a stirred suspension of 1.31 g (8.5 mmol) of silver nitrite in 5 ml of ether at 0° C. The resulting mixture was stirred under nitrogen at 0° C. for 7 hours, warmed to room temperature and stirred for an additional 16 hours. Another 1.0 g of silver nitrite was added and stirring was continued for another 20 hours.

The reaction mixture was filtered and the filtrate was concentrated to leave a residue which was purified by flash chromatography on silica gel (230-400 mesh) by elution with methylene chloride/hexane (1:4, v/v) to give, first, the recovered starting bromide, then the desired product, (0.64 g, 2.12 mmol, 78%). nmr (CDCl3) δ: 1.8-2.2 (2H, m), 2.30 (6H, a methyl singlet and a methyl doublet), 2.33 (3H, s), 2.5-2.7 (2H, m), 4.18 (2H, t, J=6Hz), 6.88 (H, bs), 7.0-7.2 (4H, m). IR (neat) 1550, 1500 cm$^{-1}$.

Step E: Preparation of Methyl 3-[2-(4'-fluoro-3,3',5-trimethyl[1,1'-biphenyl]-2-yl)ethyl]-4,5-dihydro-5-isoxazoleacetate A solution of 0.1 g (1.0 mmol) of methyl 3-butenoate and 0.174 ml (1.6 mmol) of phenyl isocyanate in 1 ml of toluene was added with stirring to a solution of 0.240 g (0.8 mmol) of the nitropropyl compound from Step D and 2 drops of triethylamine in 1 ml of toluene. The resulting mixture was stirred at room temperature for 3 hours. Additional quantities of methyl 3-butenoate (0.1 ml), triethylamine (0.1 ml) and phenyl isocyanate (0.15 ml) were added successively and stirring was continued overnight (18 hours). The mixture was filtered and the filtrate was concentrated in vacuo to a residue which was purified by flash chromatography on silica gel (230-400 mesh), first being eluted with methylene chloride to remove the impurities. Continued elution with acetone/methylene chloride (1:50, v/v) gave the desired product (0.218 g, 0.57 mmol, 71%) as a pale viscous oil. nmr (CDCl3) δ: 2.28 (6H, s), 2.32 (3H, s), 2.2-3.0 (6H, m), 3.70 (3H, s), 4.6-5.0 (H, m), 6.85 (H, bs), 7.0-7.2 (4H, m). IR (neat) 1735 cm-1

Analysis calculated for C 72.04; H, 6.83; N, 3.65. Found: C, 72.35; H, 6.99; N, 3.88.

Step F: Preparation of Methyl 7-(4'-fluoro-3,3',5-trimethyl-[1,1'-biphenyl]-2-yl)-3-hydroxy-5-oxoheptanoate A mixture of 0.1 g (0.26 mmol) of the isoxazoline from Step E, 50 mg of 10% palladium on carbon catalyst and 48 mg (0.78 mmol) of boric acid in 3 ml of methanol and 0.3 ml of water was stirred under hydrogen (1 atmosphere) at room temperature for 2.5 hours. The mixture was filtered and the filtrate was poured into brine and extracted with ether. The ethereal extract was washed with 5% (w/v) aqueous sodium bicarbonate solution, dried (MgSO4), filtered and evaporated to dryness to give 92 mg (0.23 mmol, 89%) as a pale yellow oil. nmr (CDCl3) δ: 2.30 (6H, a methyl singlet and a methyl doublet), 2.33 (3H, s), 2.35-2.5 (6H, m), 2.75-2.85 (2H, m), 3.30 (H, d), 3.70 (3H, s), 4.37 (H, m), 6.83 (H, bs), 6.95-7.1 (4H, m). IR (neat) 3450, 1710 cm$^{-1}$.

Step G: Preparation of 7-(4'-fluoro-3,3',5-trimethyl-[1,1'-biphenyl]-2-yl)-3-hydroxy-5-oxoheptanoic acid Employing the procedure substantially as described in Example 1, Step E, the ester from Step G of this Example 2 is saponified to the subject 5-keto acid.

Employing the procedure substantially as described in Example 2, Steps A through G, but substituting for the chloromethylbiphenyl employed in Step A thereof, equimolar amounts of the chloromethyl compounds described in Table II, there are produced the 5-keto esters, salts and acids also described in Table II in accordance with the following reaction sequence:

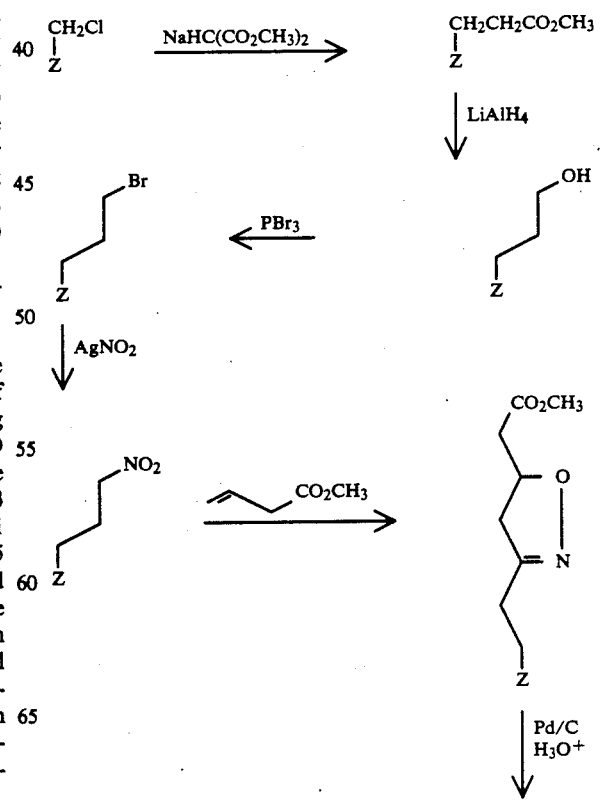

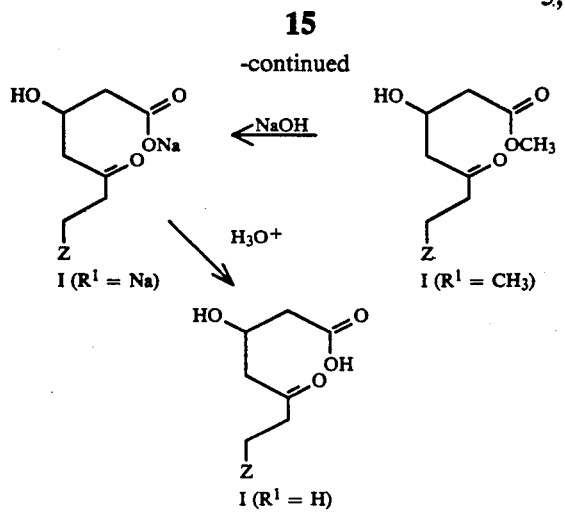

TABLE II

| | |
|---|---|
| E= | R¹⁰—⟨phenyl⟩—R¹¹ |
| Z | R¹² |

| R¹⁰ | R¹¹ | R¹² |
|---|---|---|
| 6-(4-fluorophenyl)- | 2-chloro | 4-chloro |
| 6-(4-chlorophenyl)- | 2-chloro | 4-chloro |
| 6-(3,4-dichlorophenyl)- | 2-chloro | 4-chloro |
| 6-(4-fluoro-3-methylphenyl)- | 2-chloro | 4-chloro |
| 6-(3,4-dichlorophenyl)- | 2-methyl | 4-methyl |
| 6-(3,4-dimethylphenyl)- | 2-chloro | 4-chloro |
| 6-(3,4-dichlorophenyl)- | 2-methyl | 5-methyl |
| 6-(4-fluorophenyl)- | 2-methyl | 4-methyl |
| 6-(4-fluoro-3-methylphenyl)- | 2-methyl | 4-chloro |
| 6-(4-fluorobenzyloxy) | 2-chloro | 4-chloro |
| 6-(4-fluoro-3-methylphenyl)- | 2-chloro | 4-methyl |

| | |
|---|---|
| E= | ⟨decalin⟩—(R¹⁴)ₙ |
| Z | |

| n | R¹⁴ | |
|---|---|---|
| 1 | 2-methyl | naphthyl |
| 0 | — | naphthyl |
| 2 | 2,6-dimethyl | naphthyl |
| 1 | 2-methyl | 5,6,7,8-tetrahydronaphthyl |

EXAMPLE 3

7-(2,4-Dichlorophenyl)-3-hydroxy-5-oxoheptanoic acid

Step A: Preparation of Methyl 7-(2,4-Dichlorophenyl)-3-hydroxy-5-oxo-6-heptenoate Activated manganese dioxide (40 g) was added to a solution of methyl 7-(2,4-dichlorophenyl)-3,5-dihydroxy-6-heptenoate (6.8 g, 21.3 mmol) in chloroform (600 mL) and the black suspension was vigorously stirred at ambient temperature for 20 hours. After filtration and evaporation of the solvent the residual amber oil (4.5 g, 1 major spot on TLC with Rf 0.61 on Whatman MK6F silica using CHCl -MeOH; 19:1 as eluent) was chromatographed on a Still column to obtain the product (3.9 g, 58%) as a pale yellow oil which solidified on standing, m.p. 77°–79° C.; NMR (CDCl₃) δ: 2.57 (2H, d, J=6Hz, —C₂CO₂—), 2.93 (2H, d, J=6Hz, —CH₂—CO—), 3.70 (3H, s, —CO₂CHp₃), 4.4–4.8 (H, m, —CH(OH)—), 6.67 (H, d, J=16 Hz, =CH—CO), 7.1–7.7 (3H, m. ArH), 7.93 (H, d, J=16 Hz, =CH).

Analysis for $C_{14}H_{14}Cl_2O_4$. Calcd.: C, 53.02; H, 4.45. Found: C, 53.25; H, 4.50.

Step B: Preparation of Methyl 7-(2,4-Dichlorophenyl)-3-hydroxy-5-oxoheptanoate

Tributyltin hydride (450 μL, 1.7 mmol) was added dropwise over 1-1/2 hours to a stirred solution of the ene-one ester from Step A (320 mg, 1 mmol) and tetrakis(triphenylphosphine)palladium(0) (35 mg, 0.03 mmol) in dry THF (5 mL) at ambient temperature under N₂. After standing at 20° C. overnight the light-brown solution was distributed between water (100 mL) and ether (150 mL). The organic layer was separated and washed with water (2×100 mL), dried and evaporated. The residual oil (1 major spot on TLC with Rf 0.39 vis-a-vis 0.35 for the starting ene-one ester on Whatman MK6F silica using CHCl₃-MeOH; 99:1 as eluent) was chromatographed on a Still column to obtain the product (260 mg, 81%) as a pale amber gum; NMR (CDCl₃) δ: 2.5–2.525 (2H, m, —C₂CO₂—), 2.57–2.73 (2H, m, —COC₂C(OH)—), 2.77 (2H, t, J=7.5 Hz, AR-CH₂CH₂CO-), 2.98 (2H, t, J=7.5 Hz, Ar-CH₂CH₂CO-), 3.71 (3H, s, —CO₂C₃), 4.45–4.51 (H, m, —CH(OH)—).

Analysis for $C_{14}H_{16}Cl_2OI_4$. Calcd.: C, 52.68, H, 5.05. Found: C, 52.47; H, 5.20.

Step C: Preparation of 7-(2,4-dichlorophenyl)-3-hydroxy-5-oxoheptanoic acid

Employing the procedure substantially as described in Example 1, Step E, the ester from Step B of this Example 3 is saponified to the subject 5-oxo acid.

What is claimed is:

1. A compound of structural formula:

wherein:
R¹ is
  (1) hydrogen,
  (2) C₁₋₄alkyl,
  (3) 2,3-dihydroxypropyl,
  (4) alkali metal cation, or
  (5) ammonium of formula NR³R⁴R⁵R⁶ wherein R³, R⁴, R⁵ and R⁶ are independently hydrogen or C₁₋₄ alkyl or joined together to form a 5- or 6-membered heterocycle with the nitrogen to which they are attached;

E is —CH₂CH₂, —CH=CH—, or (CH₂)₃—; and

Z is

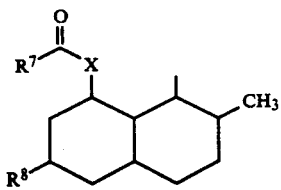    1)

wherein X is —O— or —NR⁹ wherein R⁹ is hydrogen or $C_{1-3}$alkyl;
R⁷ is $C_{2-8}$ alkyl;
R⁸ is hydrogen or —CH₃;

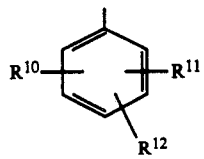    2)

wherein R are independently
a) hydrogen,
b) halogen, such as bromo, chloro or fluoro,
c) $C_{1-4}$alkyl,
d) halo-$C_{1-4}$alkyl,
e) phenyl either unsubstituted or substituted with one or more of
   i) $C_{1-4}$alkoxy,
   ii) $C_{1-4}$alkyl,
   iii) $C_{2-8}$alkanoyloxy,
   iv) halo-$C_{1-4}$alkyl, or
   v) halo,
f) OR¹³ wherein R¹³ is
   i) hydrogen,
   ii) $C_{2-8}$alkanoyl,
   iii) benzoyl,
   iv) phenyl,
   v) halophenyl,
   vi) phenyl-$C_{1-3}$alkyl, either unsubstituted or substituted with one or more of halogen, $C_{1-4}$alkoxy, $C_{1-4}$alkyl or halo-$C_{1-4}$alkyl,
   vii) $C_{1-9}$alkyl,
   viii) cinnamyl,
   ix) halo-$C_{1-4}$alkyl,
   x) allyl,
   xi) $C_{3-6}$cycloalkyl-$C_{1-3}$alkyl, or
   xii) adamantyl-$C_{1-3}$alkyl;

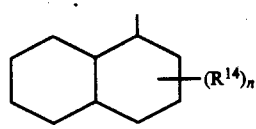    3)

wherein n is 0-2 and R¹⁴ is halo or $C_{1-4}$ alkyl; or

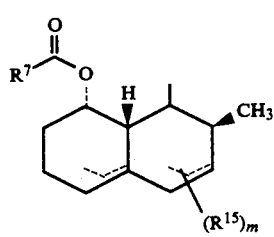    4)

wherein the dotted lines represent possible double bonds there being 0, 1 or 2 double bonds;
m represents 1, 2 or 3; and
R¹⁵ is
1) methyl,
2) hydroxy,
3) $C_{1-4}$ alkoxy,
4) oxo, or
5) halo.

2. The compound of claim 1 wherein:
R¹ is hydrogen, an alkali metal cation or an ammonium cation;
E is —CH=CH— or —CH and
Z is

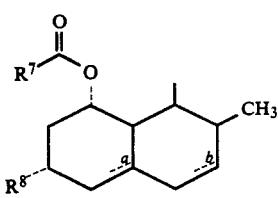    1)

wherein

is 2(S)-methylbutyryl or 2,2-dimethylbutyryl;

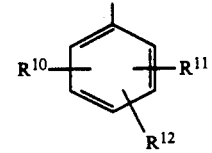    2)

wherein R¹⁰, R¹¹ and R¹² are independently
a) halogen,
b) $C_{1-4}$alkyl,
c) halo-$C_{1-4}$alkyl,
d) phenyl with 1 to 3 substituents selected from halo, $C_{1-4}$alkyl or Cl alkoxy, 1-, wherein R¹³ is
e) OR
   i) phenyl,
   ii) halophenyl, or
   iii) phenyl substituted with 1-3 substituents selected from halogen and $C_{1-4}$alkyl,
   iv) phenyl-$C_{1-3}$ alkyl, either unsubstituted or substituted with one or more of halogen, $C_{1-4}$ alkoxy, $C_{1-4}$ alkyl or halo-$C_{1-4}$ alkyl; or

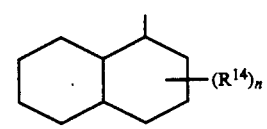    3)

wherein n is 0, 1 or 2, and is methyl, and the ring system is naphthyl, or 5,6,7,8-tetrahydronaphthyl.

3. The compound of claim 2 selected from:

| R⁷C(=O)— | R⁸ | X | a* | b |
|---|---|---|---|---|
| 2(S)-methylbutyryl | —CH₃ | O | single | double |
| 2(S)-methylbutyryl | —CH₃ | O | single | single |
| 2(R)-methylbutyryl | —CH₃ | O | double | double |
| 2,2-dimethylbutyryl | —CH₃ | O | double | double |
| 2,2-dimethylbutyryl | —CH₃ | O | single | double |
| 2,2-dimethylbutyryl | —CH₃ | O | single | single |
| acetyl | —CH₃ | O | double | double |
| 2(S)-methylbutyryl | H | O | double | double |
| 2(S)-methylbutyryl | H | O | single | single |
| 2,2-dimethylbutyryl | H | O | double | double |
| 2,2-dimethylbutyryl | H | O | single | single |
| 2,2-dimethylbutyryl | —CH₃ | NH | single | single |
| 2-methyl-2-ethyl-butyryl | —CH₃ | NH | single | single |
| 2-methylbutyryl | —CH₃ | NH | single | single |
| 4-fluorobenzoyl | —CH₃ | NH | single | single |
| 4-fluorophenyl-acetyl | —CH₃ | NH | single | single |
| 4-tert-butylbenzoyl | —CH₃ | NH | single | single |
| acetyl | —CH₃ | NH | double | double |
| acetyl | —CH₃ | NCH₃ | single | single |
| 2,2-dimethylbutyryl | —CH₃ | NCH₃ | single | single |
| 2,2-dimethylbutyryl | —CH₃ | NH | double | double |

*When a = single bond, the rings are trans-fused.

| R¹⁰ | R¹¹ | R¹² |
|---|---|---|
| 6-(4-fluoro-3-methylphenyl)- | 2-methyl | 4-methyl |
| 6-(4-fluorophenyl)- | 2-chloro | 4-chloro |
| 6-(4-chlorophenyl)- | 2-chloro | 4-chloro |
| 6-(3,4-dichlorophenyl)- | 2-chloro | 4-chloro |
| 6-(4-fluoro-3-methylphenyl)- | 2-chloro | 4-chloro |
| 6-(3,4-dichlorophenyl)- | 2-methyl | 4-methyl |
| 6-(3,5-dimethylphenyl)- | 2-chloro | 4-chloro |
| 6-(3,4-dichlorophenyl)- | 2-methyl | 5-methyl |
| 6-(4-fluorophenyl) | 2-methyl | 4-methyl |
| 6-(4-fluoro-3-methylphenyl)- | 2-methyl | 4-chloro |
| 6-(4-fluorobenzyloxy) | 2-chloro | 4-chloro |
| 6-(4-fluoro-methylphenyl) | 2-chloro | 4-methyl |

| n | R¹⁴ | |
|---|---|---|
| 1 | 2-methyl | naphthyl |
| 0 | — | naphthyl |
| 2 | 2,6-dimethyl | naphthyl |
| 1 | 2-methyl | 5,6,7,8-tetrahydronaphthyl |

4. An antihypercholesterolemic pharmaceutical composition comprising a pharmaceutical carrier and an effective antihypercholesterolemic amount of a compound as claimed in claim 1.

5. The formulation of claim 4 wherein the antihypercholesterolemic compound is as claimed in claim 9.

6. The formulation of claim 5 wherein the antihypercholesterolemic compound is as claimed in claim 10.

7. A method of treating hyperlipemia, familial hypercholesterolemia and atherosclerosis which comprises administering to a patient in need of such treatment an effective antihypercholesterolemic amount of a compound as claimed in claim 1.

8. The method of claim 7 wherein the antihypercholesterolemic compound is as claimed in claim 2.

9. The method of claim 8 wherein the antihypercholesterolemic compound is as claimed in claim 3.

* * * * *

UNITED STATES PATENT AND TRADEMARK OFFICE
CERTIFICATE OF CORRECTION

PATENT NO. : 5,053,525
DATED : October 1, 1991
INVENTOR(S) : Hoffman, W.F.; Lee, T.J.; Stokker, G.E.

It is certified that error appears in the above-identified patent and that said Letters Patent is hereby corrected as shown below:

Column 3, line 15, ">NR$^9$" should read -- -NR$^9$--.
Column 3, line 17, "C$_{2-alkyl}$" should read --C$_{2-8}$alkyl--.
Column 3, line 42, "wherein R$^{13}$" should read --OR$^{13}$ wherein R$^{13}$--.
Column 3, line 45, "C1" should read --C$_{1-8}$alkanoyl--.
Column 3, lines 1 through 9, the formula should appear as

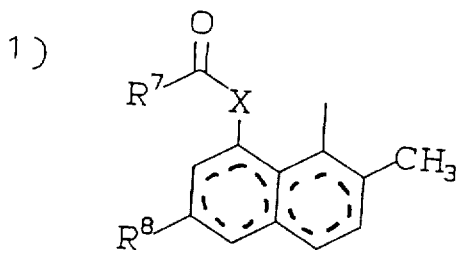

Column 3, lines 59-66, the formula should appear as

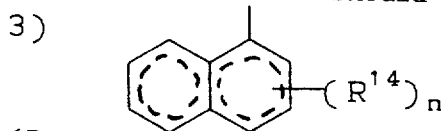

Column 3, line 67, "and is halo" should read --and R$^{14}$ is halo--.
Column 4, line 24 "hydro9en" should read --hydrogen--.
Column 4, line 60 "Rhu 13" should read --R$^{13}$--.
Column 5, lines 1-7, the formula should appear as:

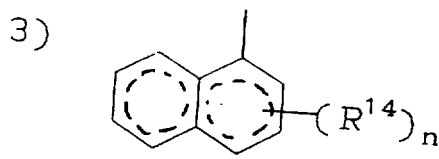

UNITED STATES PATENT AND TRADEMARK OFFICE
CERTIFICATE OF CORRECTION

PATENT NO. : 5,053,525

DATED : October 1, 1991

INVENTOR(S) : Hoffman, W.F.; Lee, T.J.; Stokker, G.E.

It is certified that error appears in the above-identified patent and that said Letters Patent is hereby corrected as shown below:

Column 5, line 9 "and is methyl" should read --and $R^{14}$ is methyl--.

Column 17, lines 1 through 9, the formula should appear as

1) 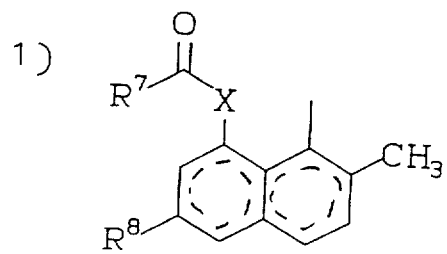

Column 17, line 22, "R are" should read --$R^{10}$, $R^{11}$, and $R^{12}$ are --.

Column 17, lines 49 - 56, the formula should appear as:

3) 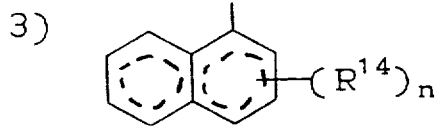

Column 18, line 10, "5 5)" should read --5)--.

Column 18, line 14 "or - CH" should read --or-$CH_2CH_2$-;--.

Column 18, line 48, "or Cl alkoxy, 1-, wherein $R^{13}$ is" should read --or $C_{1-4}$ alkoxy,--.

Column 18, line 49, "OR" should read --$OR^{13}$, wherein $R^{13}$ is--.

Column 18, lines 59-64, the formula should appear as:

UNITED STATES PATENT AND TRADEMARK OFFICE
CERTIFICATE OF CORRECTION

PATENT NO. : 5,053,525

DATED : October 1, 1991

INVENTOR(S) : Hoffman, W.F.; Lee, T. J.; Stokker, G.E.

It is certified that error appears in the above-identified patent and that said Letters Patent is hereby corrected as shown below:

3) 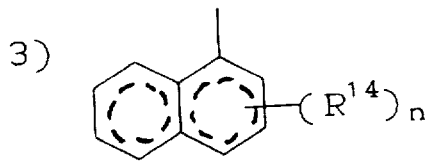

Column 18, line 65 "and is methyl" should read --and $R^{14}$ is methyl--.
Column 20, lines 29-40, the structure should appear as:

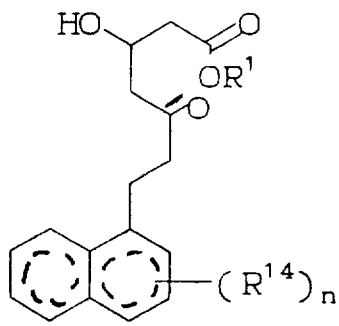

UNITED STATES PATENT AND TRADEMARK OFFICE
CERTIFICATE OF CORRECTION

PATENT NO. : 5,053,525
DATED : October 1, 1991
INVENTOR(S) : Hoffman, W.F.; Lee, T.J.; Stokker, G.E.

It is certified that error appears in the above-indentified patent and that said Letters Patent is hereby corrected as shown below:

Column 20, line 40-43, the structure should appear as:

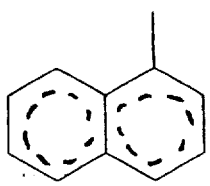

Signed and Sealed this

Nineteenth Day of April, 1994

BRUCE LEHMAN

Attest:

Attesting Officer

Commissioner of Patents and Trademarks